United States Patent [19]

Cho-Chung

[11] Patent Number: 5,627,158
[45] Date of Patent: May 6, 1997

[54] ANTISENSE OLIGONUCLEOTIDES OF HUMAN REGULATORY SUBUNIT RI-$_\alpha$ OF CAMP DEPENDENT PROTEIN KINASES FOR THE TREATMENT OF CANCER

[76] Inventor: Yoon S. Cho-Chung, 7017 Kenhill Rd., Bethesda, Md. 20817

[21] Appl. No.: 60,984

[22] Filed: May 14, 1993

Related U.S. Application Data

[60] Division of Ser. No. 702,163, May 20, 1991, Pat. No. 5,271,941, which is a continuation-in-part of Ser. No. 680,198, Apr. 5, 1991, abandoned, which is a continuation-in-part of Ser. No. 607,113, Nov. 2, 1990, abandoned.

[51] Int. Cl.$^6$ .......................... A61K 48/00; C07H 21/04; C07H 21/02; C12Q 1/68
[52] U.S. Cl. .................. 514/44; 435/6; 536/24.5
[58] Field of Search ..................... 514/44; 536/24.5; 935/33, 34, 9, 11, 13, 5, 6, 8; 435/6, 240.2

[56] References Cited

U.S. PATENT DOCUMENTS

| | | | |
|---|---|---|---|
| 5,087,617 | 2/1992 | Smith | 514/44 |
| 5,097,026 | 3/1992 | Jahnsen | 536/27 |
| 5,098,890 | 3/1992 | Gewirtz et al. | 514/44 |

FOREIGN PATENT DOCUMENTS

| | | |
|---|---|---|
| WO9000624 | 1/1990 | WIPO. |
| WO9009180 | 8/1990 | WIPO. |

OTHER PUBLICATIONS

Tortora, G. and Cho–Chung, Y.S., Type II Regulatory Subunit of Protein Kinase Restores cAMP–dependent Transcription in a cAMP–unresponsive Cell Line, *J. Biol. Chem.* 265(30):18067–18070 (Oct. 25, 1990).

Tortora, G. et al., Induction of megakaryocytic differentiation and modulation of protein kinase gene expression by site–selective cAMP analogs in K–562 human leukemic cells, *Proc. Natl. Acad. Sci. USA* 86:2849–2852 (Apr. 1989).

Tortora, G. et al., A RI$\alpha$ subunit antisense oligodeoxynucleotide of cAMP–dependent protein kinase inhibits proliferation of human HL–60 promyelocytic leukemia, *Proc. Am. Assoc. Canc. Res. Annu. Meet.* 31:38 (1990), Abstract No. 220.

Tortora, G. et al., Site–Selective cAMP Analogs at Micromolar Concentrations Induce Growth Arrest and Differentiation of Acute Promyelocytic, Chronic Myelocytic, and Acute Lymphocytic Human Leukemia Cell Lines, *Blood* 71(1):230–233 (Jan. 1988).

Taylor, S.S., et al., cAMP–dependent protein kinase: prototype for a family of enzymes, *FASEB J.* 2:2677–2685 (1988).

Tortora, G. et al., An antisense oligodeoxynucleotide targeted against the type II$_\beta$ regulatory subunit mRNA of protein kinase inhibits cAMP–induced differentiation in HL–60 leukemia cells without affecting phorbol ester effects, *Proc. Natl. Acad. Sci. USA* 87:705–708 (Jan. 1990).

Tortora, G., et al., Differentiation of HL–60 leukemia by type I regulatory subunit antisense oligodeoxynucleotide of cAMP–dependent protein kinase, *Proc. Natl. Acad. Sci. USA* 88:2011–2015 (Mar. 1991).

Stein, C.A. and Cohen, J.S., Phosphorothioate Oligodeoxynucleotide Analogues, in Oligodeoxynucleotides: Antisense Inhibitors of Gene Expression, Cohen, ed., pp. 97–117, Boca Raton, Florida, CRC Press, Inc. (1989).

Sugden, P.H., and Corbin, J.D., Adenosine 3':5'–Cyclic Monophosphate–Binding Proteins in Bovine and Rat Tissues, *Biochem. J.* 159:423–437 (1976).

Tagliaferri, P. et al., Reverse Transformation of Harvey Murine Sarcoma Virus–transformed NIH/3T3 Cells by Site-–selective Cyclic AMP Analogs, *J. Biol. Chem.* 263(1):409–416 (Jan. 5, 1988).

Schwartz, D.A. and Rubin, C.S., Identification and Differential Expression of Two Forms of Regulatory Subunits (RII) of cAMP–dependent Protein Kinases II in Friend Erythroleukemic Cells, *J. Biol. Chem.* 260(10):6296–6303 (May 25, 1985).

Scott, J.D. et al., The molecular cloning of a type II regulatory subunit of the cAMP–dependent protein kinase from rat skeletal muscle and mouse brain, *Proc. Natl. Acad. Sci. USA* 84:5192–5196 (Aug. 1987).

Stein, C.A. and Cohen, J.S., Oligodeoxynucleotides as Inhibitors of Gene Expression: A Review, *Canc. Res.* 48:2659–2668 (May 15, 1988).

Potera, C., 'Reverse Transformation' Studies Provide Clues for Treating Malignancies, *Genetic Engineering News* 5(8):20 (Sep. 1985).

Robinson–Steiner, A.M. and Corbin, J.D., Probable Involvement of Both Intrachain cAMP Binding Sites in Activation of Protein Kinase, *J. Biol. Chem.* 258(2):1032–1040 (Jan. 25, 1983).

Sandberg, M. et al., Molecular Cloning, cDNA Structure and Deduced Amino Acid Sequence for a Type I Regulatory Subunit of cAMP–Dependent Protein Kinase from Human Testis, *Biochem. Biophys. Res. Comm.* 149(3):939–945 (Dec. 31, 1987).

Øgreid, D. et al., Activation of protein kinase isozymes by cyclic nucleotide analogs used singly or in combination: Principles for optimizing the isozyme specificity of analog combinations, *Eur. J. Biochem.* 150:219–227 (1985).

Øyen, O. et al., Human testis cDNA for the regulatory subunit $RII_\alpha$ of cAMP–dependent protein kinase encodes an alternate amino–terminal region, *FEBS Letts.* 246(1,2):57–64 (Mar. 1989).

Paterson, B.M. et al., Structural gene identification and mapping by DNA•mRNA hybrid–arrested cell–free translation, *Proc. Natl. Acad. Sci. USA* 74(10):4370–4374 (Oct. 1977).

Lee, D.C. et al., Isolation of a cDNA clone for the type I regulatory subunit of bovine cAMP–dependent protein kinase, *Proc. Natl. Acad. Sci. USA* 80:3608–3612 (Jun. 1983).

Levy, F.O., et al., Molecular Cloning, Complementary Deoxyribonucleic Acid Structure and Predicted Full–Length Amino Acid Sequence of the Hormone–Inducible Regulatory Subunit of 3'–5'–Cyclic . . . , *Mol. Endo.* 2(12):1364–1373 (1988).

Mizuno, T. et al., A unique mechanism regulating gene expression: Translational inhibition by a complementary RNA transcript (micRNA), *Proc. Natl. Acad. Sci. USA* 81:1966–1970 (Apr. 1984).

Iyer, R.P. et al., 3H–1,2–Benzodithiole–3–one 1,1–Dioxide as an Improved Sulfurizing Reagent in the Solid–Phase Synthesis of Oligodeoxyribonucleoside Phosphorothioates, *J. Am. Chem. Soc.* 112:1253–1254 (1990).

Jahnsen, T., et al., Molecular Cloning, cDNA Structure, and Regulation of the Regulatory Subunit of Type II cAMP–dependent Protein Kinase from Rat Ovarian Granulosa Cells, *J. Biol. Chem.* 261(26):12352–12361 (Sep. 15, 1986).

Katsaros, D. et al., Site–selective cyclic AMP analogs provide a new approach in the control of cancer cell growth, *FEBS Letts.* 233(1):97–103 (Oct. 1987).

Corbin, J.D. et al., The Distribution and Dissociation of Cyclic Adenosine 3':5'–Monophosphate–dependent Protein Kinases in Adipose, Cardiac, and Other Tissues, *J. Biol. Chem.* 250(1):218–225 (Jan. 10, 1975).

Heywood, S.M., tcRNA as a naturally occurring antisense RNA in eukaryotes, *Nucl. Acids Res.* 14(16):6771–6772 (1986).

Hofmann, F. et al., Concentrations of Cyclic AMP–dependent Protein Kinase Subunits in Various Tissues, *J. Biol. Chem.* 252(4):1441–1447 (Feb. 25, 1977).

Clegg, C.H. et al., Genetic characterization of a brain–specific form of the type I regulatory subunit of cAMP–dependent protein kinase, *Proc. Natl. Acad. Sci. USA* 85:3703–3707 (Jun. 1988).

Cohen, J.S., Designing antisense oligonucleotides as pharmaceutical agents, *Trends Pharamcol. Sci.* 10(11):435–437 (1989).

Cohen, J.S., Topics in Molecular and Structural Biology, Oligodeoxynucleotides: Antisense Inhibitors of Gene Expression, Natl. Cancer Inst., Bethesda, Md. pp. 1–6, Boca Roton, Florida, CRC Press, Inc. (1989).

Cho–Chung, Y., et al., An antisense oligodeoxynucleotide targeted against the type I regulatory subunit ($RI_\alpha$) mRNA of cAMP–dependent protein kinase (PKA) inhibits the growth of LS–174T human colon carcinoma in athymic mice, *Proc. Am. Assoc. Canc. Res. Annu. Meet.* 32:277 (1991), Abstract No. 1645.

Cho–Chung, Y.S. et al., A $RI\alpha$ subunit antisense oligodeoxynucleotide of cAMP–dependent protein kinase blocks proliferation in human and rodent cancer cell lines by–passing exogenous cAMP effect, *Proc. Am. Assoc. Canc. Res. Annu. Meet.* 31:29 (1990) Abstract No. 171.

Cho–Chung, Y.S. et al., Site–Selective Cyclic AMP analogs as New Biological Tools in Growth Control, Differentiation, and Proto–oncogene Regulation, *Canc. Invest.* 7(2):161–177 (1989).

Ally, S., Selective modulation of protein kinase isozymes by the site–selective analog 8–chloroadenosine 3'5',–cyclic monophosphate provides a biological means for control of human colon cancer cell growth, *Proc. Natl. Acad. Sci. USA* 85:6319–6322 (Sep. 1988).

Campbell, J.M. et al., Oligodeoxynucleoside Phosphorothioate stability in subcellular extracts, culture media, sera and cerebrospinal fluid, *J. Biochem. Biophys. Meth.* 20:259–267 (1990).

Cho–Chung, Y.S., Site–Selective 8–Chloro–Cyclic Adenosine 3',5'–Monophosphate as a Biologic Modulator of Cancer: Restoration of Normal Control Mechanisms, *J. Natl. Canc. Inst.* 81(13):982–987 (Jul. 5, 1989).

C. Stein et al., Science, vol. 261 (20 Aug. '93) pp. 1004–1012.

B. Tseng et al., Cancer Gene Therapy, vol. 1, No. 1 (Mar. 94) pp. 65–71.

R. Weiss, Science News, vol. 139 (16 Feb. '91) pp. 108–109.

R. Phillips et al., J.N.C.I., vol. 82, No. 18(19 Sep. '90) pp. 1457–1468.

K. Smith, et al. Eur. J. Cancer Clin. Oncol., vol. 21, no. 2 ('85) pp. 249–256.

K. Zirri, et al., Cancer Letters, vol. 72 ('93) pp. 39–44.

J. Milligan et al., J. Med. Chem., vol. 36 No. 14 (9 Jul. '93) pp. 1923–1937 (Ex. 9).

E. Uhlmann et al. Chemical Reviews, vol. 90, #4 (1990) pp. 543–584.

C. Mirabelli et al. Anti–Cancer Drug Design, vol. 6 (1991) pp. 647–661.

P. Westermann et al. Biomed, Biochem. Acta, vol. 48 (1989) pp. 85–93.

J. Potts P.N.A.S., vol. 88 (1991) pp. 1516–1520.

A. Storey Nucl. Acids Res., vol. 19, #15 (1991) pp. 4109–4114.

L. Perlaky et al. Anti–Cancer Drug Design, vol. 7 (1992) pre–print.

M. Ratajczak et al. P.N.A.S., vol. 89 (1992) pp. 11823–11827.

D. Becker et al. The EMBO Journal, vol. 8, #12 ('89) pp. 3685–3691.

Y. Furukawa Science, vol. 250 (1990) pp. 805–808.

C. Szczylik et al. Science, vol. 253 ('91) pp. 562–565.

D. Jaskulski et al. Science, vol. 240 ('88) pp, 1544–1546.

S. Crooke Annu. Rev. Pharmacol. Toxicol. ('92 ) vol. 32, pp. 329–376.

*Primary Examiner*—Charles C. P. Rories
*Attorney, Agent, or Firm*—Sterne, Kessler Goldstein & Fox P.L.L.C.

[57] ABSTRACT

Antisense oligonucleotides of human regulatory subunit RI-alpha of cAMP-dependent protein kinases are disclosed along with pharmaceutical compositions containing these oligonucleotides as the active ingredients. These antisense oligonucleotides are useful for inhibiting the growth of cancer.

10 Claims, 8 Drawing Sheets

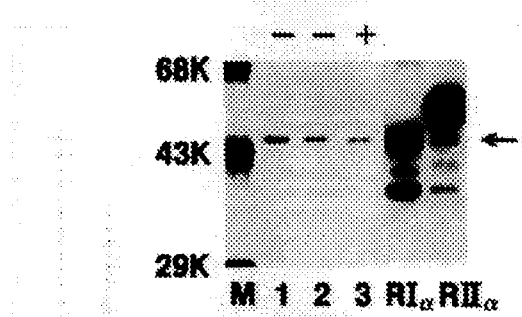
FIG.4A
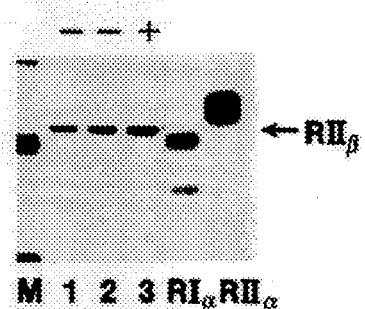
FIG.4B
| Lane | Treatment | Relative Levels | |
|---|---|---|---|
| | | RI$_\alpha$ | RII$_\beta$ |
| 1 | Control | 1.0±0.1 | 1.0±0.1 |
| 2 | 8-Cl + N$^6$-Benzyl | 0.3±0.04 | 3.0±0.3 |
| 3 | RI$_\alpha$ Antisense | 0.2±0.03 | 5.0±0.4 |
FIG.4C

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 21 bases
        ( B ) TYPE: Nucleic acid
        ( C ) STRANDEDNESS: Single
        ( D ) TOPOLOGY: Linear ( i i ) MOLECULE TYPE: DNA ( i v ) ANTI-SENSE: yes ( x i ) SEQUENCE DESCRIPTION: SEQ ID NO:1:

GGCGGTACTG CCAGACTCCA T        2 1

( 2 ) INFORMATION FOR SEQ ID NO:2:

( i ) SEQUENCE CHARACTERISTICS:
        ( A ) LENGTH: 18 bases
        ( B ) TYPE: Nucleic acid
        ( C ) STRANDEDNESS: Single
        ( D ) TOPOLOGY: linear ( i i ) MOLECULE TYPE: DNA ( i v ) ANTI-SENSE: yes ( x i ) SEQUENCE DESCRIPTION: SEQ ID NO:2:

```
GCGTGCCTCC TCACTGGC                                                   18
```

( 2 ) INFORMATION FOR SEQ ID NO:3:

( i ) SEQUENCE CHARACTERISTICS:
        ( A ) LENGTH: 21 bases
        ( B ) TYPE: Nucleic acid
        ( C ) STRANDEDNESS: Single
        ( D ) TOPOLOGY: linear ( i i ) MOLECULE TYPE: DNA ( i v ) ANTI-SENSE: yes ( x i ) SEQUENCE DESCRIPTION: SEQ ID NO:3:

```
GAGCTCACAT TCTCGAAGGC T                                               21
```

( 2 ) INFORMATION FOR SEQ ID NO:4:

( i ) SEQUENCE CHARACTERISTICS:
        ( A ) LENGTH: 21 bases
        ( B ) TYPE: Nucleic acid
        ( C ) STRANDEDNESS: Single
        ( D ) TOPOLOGY: linear ( i i ) MOLECULE TYPE: DNA ( i v ) ANTI-SENSE: yes ( x i ) SEQUENCE DESCRIPTION: SEQ ID NO:4:

```
GATAGCACCT CGTCGCCTCC T                                               21
```

( 2 ) INFORMATION FOR SEQ ID NO:5:

( i ) SEQUENCE CHARACTERISTICS:
        ( A ) LENGTH: 300 bases
        ( B ) TYPE: Nucleic acid
        ( C ) STRANDEDNESS: Single
        ( D ) TOPOLOGY: linear ( i i ) MOLECULE TYPE: DNA ( i v ) ANTI-SENSE: yes ( x i ) SEQUENCE DESCRIPTION: SEQ ID NO:5:

```
GATAGCACCT CGTCGCCTCC TACCTTTAAC CACTGGGTTG GGTGGAGGAG GAGAAATCTC   60
ATCCTCCCTT GAGTCTGTAC GAGTGCCTGC TTTCTGCAGA TTGTGAATCT GTTTTGCCTC  120
CTCCTTCTCC AACCTCTCAA AGTATTCCCT GAGGAATGCC ATGGACTCT  CAGGTCGAGC  180
AGTGCACAAC TGCACAATAG AATCTTTGAG CAGTGCTTGA ATGTTATGCT TCTGGACGTA  240
GAGCTCACAT TCTCGAAGGC TGCGTGCCTC CTCACTGGCG GCGGTACTGC CAGACTCCAT  300
```

( 2 ) INFORMATION FOR SEQ ID NO:6:

( i ) SEQUENCE CHARACTERISTICS:
        ( A ) LENGTH: 300 bases (B) TYPE: Nucleic acid
        (C) STRANDEDNESS: Single
        (D) TOPOLOGY: linear (ii) MOLECULE TYPE: DNA (iv) ANTI-SENSE: no (xi) SEQUENCE DESCRIPTION: SEQ ID NO:6:

ATGGAGTCTG GCAGTACCGC CGCCAGTGAG GAGGCACGCA GCCTTCGAGA ATGTGAGCTC 60

TACGTCCAGA AGCATAACAT TCAAGCACTG CTCAAAGATT CTATTGTGCA GTTGTGCACT 120

GCTCGACCTG AGAGACCCAT GGCATTCCTC AGGGAATACT TTGAGAGGTT GGAGAAGGAG 180

GAGGCAAAAC AGATTCAGAA TCTGCAGAAA GCAGGCACTC GTACAGACTC AAGGGAGGAT 240

GAGATTTCTC CTCCTCCACC CAACCCAGTG GTTAAAGGTA GGAGGCGACG AGGTGCTATC 300

(2) INFORMATION FOR SEQ ID NO:7:

(i) SEQUENCE CHARACTERISTICS:
        (A) LENGTH: 21 bases
        (B) TYPE: Nucleic acid
        (C) STRANDEDNESS: Single
        (D) TOPOLOGY: linear (ii) MOLECULE TYPE: DNA (iv) ANTI-SENSE: No (xi) SEQUENCE DESCRIPTION: SEQ ID NO:7:

CGATCGATCG ATCGATCGTA C     21

ANTISENSE OLIGONUCLEOTIDES OF HUMAN REGULATORY SUBUNIT RI-$\alpha$ OF CAMP DEPENDENT PROTEIN KINASES FOR THE TREATMENT OF CANCER The present invention was made with government support. Accordingly, the United States government has certain rights in the invention.

CROSS-REFERENCE TO RELATED APPLICATION

This application is a division of application Ser. No. 07/702,163, filed May 20, 1991, now U.S. Pat. No. 5,271,941, which is a continuation-in-part of U.S. application Ser. No. 07/680,198, abandoned, filed Apr. 5, 1991, which is a continuation-in-part of U.S. application Ser. No. 07/607,113, filed Nov. 2, 1990 abandoned, the contents of which are fully incorporated by reference herein.

FIELD OF THE INVENTION

The invention is in the field of medicinal chemistry. In particular, the invention relates to certain antisense oligonucleotides and the use thereof for the treatment of cancer.

BACKGROUND OF THE INVENTION

Control mechanisms for cell growth and differentiation are disrupted in neoplastic cells (Potter, V. R. (1988) *Adv. Oncol.* 4, 1–8; Strife, A. & Clarkson, B. (1988) *Semin. Hematol.* 25, 1–19; Sachs, L. (1987) *Cancer Res.* 47, 1981–1986). cAMP, an intracellular regulatory agent, has been considered to have a role in the control of cell proliferation and differentiation (Pastan, I., Johnson, G. S. & Anderson, W. B. (1975) *Ann. Rev. Biochem.* 44, 491–522; Prasad, K. N. (1975) *Biol. Rev.* 50, 129–165; Cho-Chung, Y. S. (1980) *J. Cyclic Nucleotide Res.* 6, 163–177; Puck, T. T. (1987) *Somatic Cell Mot. Genet.* 13, 451–457). Either inhibitory or stimulatory effects of cAMP on cell growth have been reported previously in studies in which cAMP analogs such as $N^6$-$O^{2'}$-dibutyryladenosine 3',5'-cyclic monophosphate or agents that raise intracellular cAMP to abnormal and continuously high levels were used, and available data are interpreted very differently (Chapowski, F. J., Kelly, L. A. & Butcher, R. W. (1975) *Adv. Cyclic Nucleotide Protein Phosphorylat. Res.* 6, 245–338; Cho-Chung, Y. S. (1979) in *Influence of Hormones on Tumor Development*, eds. Kellen, J. A. & Hilf, R. (CRC, Boca Raton, Fla.), pp. 55–93); Prasad, K. N. (1981) in *The Transformed Cell*, eds. Cameron, L. L. & Pool, T. B. (Academic, New York), pp. 235–266; Boynton, A. L. & Whitfield, J. F. (1983) *Adv. Cyclic Nucleotide Res.* 15, 193–294).

Recently, site-selective cAMP analogs were discovered which show a preference for binding to purified preparations of type II rather than type I cAMP-dependent protein kinase in vitro (Robinson-Steiner, A. M. & Corbin, J. D. (1983) *J. Biol. Chem.* 258, 1032–1040; Øgreid, D., Ekanger, R., Suva, R. H., Miller, J. P., Sturm, P., Corbin, J. D. & Døskeland, S. O. (1985) *Eur. J. Biochem.* 150, 219–227), provoke potent growth inhibition, differentiation, and reverse transformation in a broad spectrum of human and rodent cancer cell lines (Katsaros, D., Tortora, G., Tagliaferri, P., Clair, T., Ally, S., Neckers, L., Robins, R. K. & Cho-Chung, Y. S. (1987) *FEBS Lett.* 223, 97–103; Tortora, G., Tagliaferri, P., Clair, T., Colamonici, O., Neckers, L. M., Robins, R. K. & Cho-Chung, Y. S. (1988) *Blood,* 71, 230–233; Tagliaferri, P., Katsaros, D., Clair, T., Robins, R. K. & Cho-Chung, Y. S. (1988) *J. Biol. Chem.* 263, 409–416). The type I and type II protein kinases are distinguished by their regulatory subunits (RI and RII, respectively) (Corbin, J. D., Keely, S. L. & Park, C. R. (1975) *J. Biol. Chem.* 250, 218–225; Hofmann, F., Beavo, J. A. & Krebs, E. G. (1975) *J. Biol. Chem.* 250, 7795–7801). Four different regulatory subunits [RI$_\alpha$ (previously designated RI) (Lee, D. C., Carmichael, D. F., Krebs, E. G. & McKnight, G. S. (1983) *Proc. Natl. Acad. Sci. USA* 80, 3608–3612), RI$_\beta$ (Clegg, C. H., Cadd, G. G. & McKnight, G. S. (1988) *Proc. Natl. Acad. Sci. USA* 85, 3703–3707), RII$_\alpha$ (RII$_{54}$) (Scott, J. D., Glaccum, M. B., Zoller, M. J., Uhler, M. D., Hofmann, D. M., McKnight, G. S. & Krebs, E. G. (1987) *Proc. Natl. Acad. Sci. USA* 84, 5192–5196) and RII$_\beta$ (RII$_{51}$) (Jahnsen, T., Hedin, L., Kidd, V. J., Beattie, W. G., Lohmann, S. M., Walter, U., Durica, J., Schulz, T. Z., Schlitz, E., Browner, M., Lawrence, C. B., Goldman, D., Ratoosh, S. L. & Richards, J. S. (1986) *J. Biol. Chem.* 261, 12352–12361)] have now been identified at the gene/mRNA level. Two different catalytic subunits [C$_\alpha$ (Uhler, M. D., Carmichael, D. F., Lee, D. C. Chrivia, J. C., Krebs, E. G. & McKnight, G. S. (1986) *Proc. Natl. Acad. Sci. USA* 83, 1300–1304) and C$_\beta$ (Uhler, M. D., Chrivia, J. C. & McKnight, G. S. (1986) *J. Biol. Chem.* 261, 15360–15363; Showers, M. O. & Maurer, R. A. (1986) *J. Biol. Chem.* 261, 16288–16291)] have also been identified; however, preferential coexpression of either one of these catalytic subunits with either the type I or type II protein kinase regulatory subunit has not been found (Showers, M. O. & Maurer, R. A. (1986) *J. Biol. Chem,* 261, 16288–16291).

The growth inhibition by site-selective cAMP analogs parallels reduction in RI$_\alpha$ with an increase in RII$_\beta$, resulting in an increase of the RII$_\beta$/RI$_\alpha$ ratio in cancer cells (Ally, S., Tortora, G., Clair, T., Grieco, D., Merlo, G., Katsaros, D., Øgreid, D., Døskeland, S. O., Jahnsen, T. & Cho-Chung, Y. S. (1988) *Proc. Natl. Acad. Sci. USA* 85, 6319–6322; Cho-Chung, Y. S. (1989) J. Natl. Cancer Inst. 81, 982–987).

Such selection modulation of RI$_\alpha$ versus RII$_{62}$ is not mimicked by treatment with $N^6,O^{2'}$-dibutyryladenosine 3',5'-cyclic monophosphate, a previously studied cAMP analog (Ally, S., Tortora, G., Clair, T., Grieco, D., Merlo, G., Katsaros, D., Øgreid, D., Døskeland, S. O., Jahnsen, T. & Cho-Chung, Y. S. (1988) *Proc. Natl. Acad, Sci. USA* 85, 6319–6322). The growth inhibition further correlates with a rapid translocation of RII$_\beta$ to the nucleus and an increase in the transcription of the RII$_{62}$ gene (Ally, S., Tortora, G., Clair, T., Grieco, D., Merlo, G., Katsaros, D., Øgreid, D., Døskeland, S. O., Jahnsen, T. & Cho-Chung, Y. S. (1988) *Proc. Natl. Acad. Sci. USA* 85, 6319–6322). These results support the hypothesis that RII$_{62}$ plays an important role in the cAMP growth regulatory function (Cho-Chung, Y. S. (1989) *J. Natl. Cancer Inst.* 81, 982–987).

Antisense RNA sequences have been described as naturally occurring biological inhibitors of gene expression in both prokaryotes (Mizuno, T., Chou, M-Y, and Inouye, M. (1984), *Proc. Natl. Acad. Sci. USA* 81, (1966–1970)) and eukaryotes (Heywood, S. M. *Nucleic Acids Res.,* 14, 6771–6772 (1986)), and these sequences presumably function by hybridizing to complementary mRNA sequences, resulting in hybridization arrest of translation (Paterson, B. M., Roberts, B. E., and Kuff, E. L., (1977) *Proc. Natl. Acad. Sci. USA,* 74, 4370–4374. Antisense oligodeoxynucleotides are short synthetic nucleotide sequences formulated to be complementary to a specific gene or RNA message. Through the binding of these oligomers to a target DNA or mRNA sequence, transcription or translation of the gene can be selectively blocked and the disease process generated by that gene can be halted. The cytoplasmic location of mRNA provides a target considered to be readily accessible to antisense oligodeoxynucleotides entering the cell; hence much of the work in the field has focused on RNA as a target. Currently, the use of antisense oligodeoxynucleotides provides a useful tool for exploring regulation of gene expression in vitro and in tissue culture (Rothenberg, M., Johnson, G., Laughlin, C., Green, I., Craddock, J., Sarver, N., and Cohen, J. S. (1989) *J. Natl. Cancer Inst.*, 81:1539–1544.

SUMMARY OF THE INVENTION

The invention is related to the discovery that inhibiting the expression of $RI_\alpha$ in leukemia cells by contact with an antisense O-oligonucleotides and S-oligonucleotides for $RI_\alpha$ results in the inhibition of proliferation and the stimulation of cell differentiation. Accordingly, the invention is directed to $RI_\alpha$ antisense oligonucleotides and pharmaceutical compositions thereof for the treatment of cancer.

In particular, the invention is related to 15- to 30-mer antisense oligonucleotides which are complementary to a region in the first 100 N-terminal codons of $RI_\alpha$ (Seq. ID No:6).

The invention is also related to 15- to 30-mer antisense oligonucleotides which are a fragment of antisense DNA complementary to $RI_\alpha$ (Seq. ID No: 5).

The invention is also related to pharmaceutical compositions comprising at least one 15- to 30-mer antisense oligonucleotide which is complementary to a region in the first 100 N-terminal codons of $RI_\alpha$ (Seq. ID No:6); and a pharmaceutically acceptable carrier.

The invention is also related to a method for treating cancer by suppressing growth of cancer cells susceptible to growth suppression and for inducing cancer cell differentiation in an animal comprising administering to an animal in need of such treatment a cancer cell growth suppressing amount of an $RI_\alpha$ antisense oligonucleotide.

DESCRIPTION OF THE FIGURES

FIGS. 4A, 4B, and 4C depict SDS-PAGE showing the effect of $RI_\alpha$ antisense oligodeoxynucleotide on the basal and induced levels of $RI_\alpha$ and $RII_\beta$ cAMP receptor proteins in HL-60 leukemic cells. Cells were either exposed to $RI_\alpha$ antisense oligodeoxynucleotide (SEQ ID NO:1) (15 µM) or treated with cAMP analogs as described in FIG. 1. Preparation of cell extracts, the photoactivated incorporation of 8-$N_3$-[$^{32}$P]cAMP and immunoprecipitation using the anti-$RI_\alpha$ or anti-$RII_{62}$ antiserum and protein A Sepharose, and SDS-PAGE of solubilized antigen-antibody complex followed the methods described in the Examples. Pre-immune serum controls were carried out simultaneously and detected no immunoprecipitated band. M, $^{14}$C-labeled marker proteins of known molecular weight; $RI_\alpha$, the 48,000 molecular weight RI (Sigma); $RII_\alpha$, the 56,000 molecular weight RII (Sigma). Lanes $RI_\alpha$ and $RII_{62}$ are from photoaffinity labeling with 8-$N_3$-[$^{32}$P]cAMP only; lanes 1 to 3, photoaffinity labeling with 8-$N_3$-[$^{32}$P]cAMP followed by immunoprecipitation with anti-$RI_\alpha$ or anti-$RII_{62}$ antiserum. 8-Cl, 8-Cl-cAMP (5 µM); $N^6$-benzyl, $N^6$-benzyl-cAMP (5µM). The data in the table represent quantification by densitometric scanning of the autoradiograms. The data are expressed relative to the levels in control cells unexposed to $RI_\alpha$ antisense oligomer and untreated with cAMP analog, which are set equal to 1 arbitrary unit. The data represent an average±SD of three experiments. A and B, immunoprecipitation with anti-$RI_\alpha$ and anti-$RII_\beta$ antisera, respectively.

FIG. 7A shows the oligodeoxynucleotide concentration-dependent inhibition of tumor growth. O-oligo, $RI_\alpha$ antisense oligodeoxynucleotide; S-oligo, phosphorothioate analog of $RI_\alpha$ antisense oligomer. The cholesterol pellets (total weight 20 mg) containing the indicated doses of O-oligo or S-oligo were implanted s.c. one time, at zero time, and tumor sizes were measured. Tumor volume (see Materials and Methods, Example 3 ) represents an average±S.D. of 7 tumors. FIG. 7B shows the temporal effect of antisense oligodeoxynucleotide phosphorothioate analogs on tumor growth. S-oligos as indicated at 0.3 mg dose in cholesterol pellets (total weight 20 mg) were implanted s.c. 2×/week, and tumor volume (see Materials and Methods, Example 3 ) represents an average±S.D. of 7 tumors.

DESCRIPTION OF THE PREFERRED EMBODIMENTS

Figure 1A:
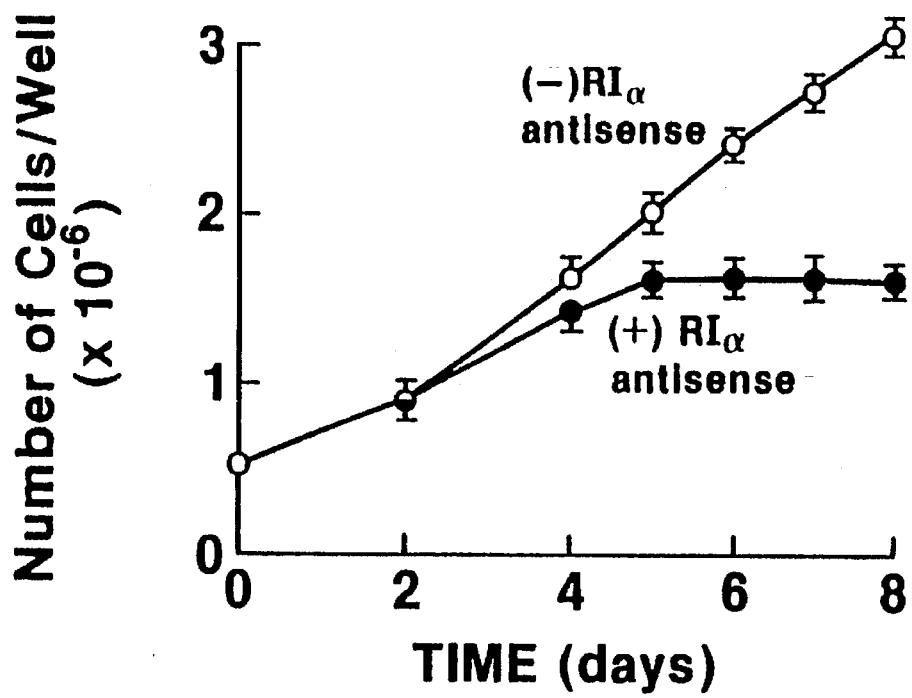
FIGS. 1A and 1B depict graphs showing the effect of $RI_\alpha$ antisense oligodeoxynucleotide (SEQ. ID NO:1) on the basal rate of growth of HL-60 leukemic cells (A) and the growth of these cells when treated with cAMP analogs or TPA (B). A, cells were grown (see the Examples) in the absence (O) or presence (●) of $RI_\alpha$ antisense oligodeoxynucleotide (15 µM). At indicated times, cell counts in duplicate were performed. Data represent the average values±SD of four experiments. B, On day 4 of experiment A, cells exposed or unexposed to $RI_\alpha$ antisense oligodeoxynucleotide (SEQ ID NO:1) were reseeded (day 0) at $5 \times 10^5$ cells/dish, and cells pre-exposed to $RI_\alpha$ antisense oligodeoxynucleotide were further treated with the oligomer at day 0 and day 2. cAMP analogs and TPA were added one time at day 0. Cell counts were performed on a Coulter counter on day 4. 8-Cl, 8-Cl-cAMP (10 µM); 8-Cl+$N^6$-B, 8-Cl-cAMP (5 µM)+$N^6$-benzyl-cAMP (5 µM); TPA ($10^{-8}$M). The data represent the average values±SD of four experiments.

Antisense therapy is the administration of exogenous oligonucleotides which bind to a target polynucleotide located within the cells. The term "antisense" refers to the fact that such oligonucleotides are complementary to their intracellular targets, e.g., $RI_\alpha$. See for example, Jack Cohen, *OLIGODEOXYNUCLEOTIDES, Antisense Inhibitors of Gene Expression*, CRC Press, 1989; and *Synthesis* 1:1–5 (1988). The $RI_\alpha$ antisense oligonucleotides of the present invention include derivatives such as S-oligonucleotides (phosphorothioate derivatives or S-oligos, see, Jack Cohen, supra) which exhibit enhanced cancer cell growth inhibitory action (see FIGS. 5 and 7A).

S-oligos (nucleoside phosphorothioates) are isoelectronic analogs of an oligonucleotide (O-oligo) in which a non-bridging oxygen atom of the phosphate group is replaced by a sulfur atom. The S-oligos of the present invention may be prepared by treatment of the corresponding O-oligos with 3H-1,2-benzodithiol-3-one-1,1-dioxide which is a sulfur transfer reagent. See Iyer, R. P. et al., *J. Org. Chem.* 55:4693–4698 (1990); and Iyer, R. P. et al., *J. Am. Chem. Soc.* 112:1253–1254 (1990), the disclosures of which are fully incorporated by reference herein.

The $RI_{60}$ antisense oligonucleotides of the present invention may be RNA or DNA which is complementary to and stably hybridizes with the first 100 N-terminal codons of the $RI_\alpha$ genome or the corresponding mRNA. Use of an oligonucleotide complementary to this region allows for the selective hybridization to $RI_\alpha$ mRNA and not to mRNA specifying other regulatory subunits of protein kinase. Preferably, the $RI_\alpha$ antisense oligonucleotides of the present invention are a 15 to 30-mer fragment of the antisense DNA molecule having SEQ ID NO:5 which hybridizes to $RI_\alpha$ mRNA. Alternatively, $RI_\alpha$ antisense oligonucleotide is a 15- to 30-mer oligonucleotide which is complementary to a region in the first 100 N-terminal codons of $RI_\alpha$ (Seq. ID No:6). Most preferably, the $RI_\alpha$ antisense oligonucleotide has SEQ ID No:1, SEQ ID No:2, SEQ ID No:3, or SEQ ID No:4.

Included as well in the present invention are pharmaceutical compositions comprising an effective amount of at least one of the $RI_\alpha$ antisense oligonucleotides of the invention in combination with a pharmaceutically acceptable carrier. In one embodiment, a single $RI_\alpha$ antisense oligonucleotide is utilized. In another embodiment, two $RI_\alpha$ antisense oligonucleotides are utilized which are complementary to adjacent regions of the $RI_\alpha$ genome. Administration of two $RI_\alpha$ antisense oligonucleotides which are complementary to adjacent regions of the $RI_\alpha$ genome or corresponding mRNA may allow for more efficient inhibition of $RI_\alpha$ genomic transcription or mRNA translation, resulting in more effective inhibition of cancer cell growth.

Preferably, the $RI_\alpha$ antisense oligonucleotide is coadministered with an agent which enhances the uptake of the antisense molecule by the cells. For example, the $RI_\alpha$ antisense oligonucleotide may be combined with a lipophilic cationic compound which may be in the form of liposomes. The use of liposomes to introduce nucleotides into cells is taught, for example, in U.S. Pat. Nos. 4,897,355 and 4,394,448, the disclosures of which are incorporated by reference in their entirety. See also U.S. Pat. Nos. 4,235,871, 4,231,877, 4,224,179, 4,753,788, 4,673,567, 4,247,411, 4,814,270 for general methods of preparing liposomes comprising biological materials.

Alternatively, the $RI_\alpha$ antisense oligonucleotide may be combined with a lipophilic carrier such as any one of a number of sterols including cholesterol, cholate and deoxycholic acid. A preferred sterol is cholesterol.

In addition, the $RI_\alpha$ antisense oligonucleotide may be conjugated to a peptide that is ingested by cells. Examples of useful peptides include peptide hormones, antigens or antibodies, and peptide toxins. By choosing a peptide that is selectively taken up by the neoplastic cells, specific delivery of the antisense agent may be effected. The $RI_\alpha$ antisense oligonucleotide may be covalently bound via the 5'OH group by formation of an activated aminoalkyl derivative. The peptide of choice may then be covalently attached to the activated $RI_\alpha$ antisense oligonucleotide via an amino and sulfhydryl reactive hetero bifunctional reagent. The latter is bound to a cysteine residue present in the peptide. Upon exposure of cells to the $RI_\alpha$ antisense oligonucleotide bound to the peptide, the peptidyl antisense agent is endocytosed and the $RI_\alpha$ antisense oligonucleotide binds to the target $RI_\alpha$ mRNA to inhibit translation. See PCT Application Publication No. PCT/US89/02363.

As antineoplastic agents, the $RI_\alpha$ antisense oligonucleotides of the present invention are useful in treating a variety of cancers, including, but not limited to, gastric, pancreatic, lung, breast, anal, colorectal, head and neck neoplasms, neuroblastomas, melanoma and various leukemias.

The $RI_\alpha$ antisense oligonucleotides of the invention may also be active against the following tumor systems: F9 teratocarcinoma, SK-N-SH neuroblastoma, TMK-1 gastric carcinoma, HL-60 promyelocytic Leukemia, Leukemia L-1210, Leukemia P388, P1534 leukemia, Friend Virus Leukemia, Leukemia L4946, Mecca lymphosarcoma, Gardner lymphosarcoma, Ridgway Osteogenic sarcoma, Sarcoma 180 (ascites), Wagner osteogenic sarcoma, Sarcoma T241, Lewis lung carcinoma, Carcinoma 755, CD8F, MCF-7 breast carcinoma, Colon 38, LS-174T colon carcinoma, Carcinoma 1025, Ehrlich carcinoma (ascites & solid), Krubs 2 carcinoma (ascites), Bashford carcinoma 63, Adenocarcinoma E 0771, B16 Melanoma, Hardin-Passey melanoma, Giloma 26, Miyona adenocarcinoma, Walker carcinosarcoma 256, Flexner-Jobling carcinoma, Jensen sarcoma, Iglesias sarcoma, Iglesias ovarian tumor, Murphy-Sturn lymphosarcoma, Yoshida sarcoma, Dunning leukemia, Rous chicken sarcoma, and Crabb hamster sarcoma.

The $RI_\alpha$ antisense oligonucleotides and the pharmaceutical compositions of the present invention may be administered by any means that achieve their intended purpose. For example, administration may be by parenteral, subcutaneous, intravenous, intramuscular, intra-peritoneal, or transdermal routes. The dosage administered will be dependent upon the age, health, and weight of the recipient, kind of concurrent treatment, if any, frequency of treatment, and the nature of the effect desired.

Compositions within the scope of this invention include all compositions wherein the $RI_\alpha$ antisense oligonucleotide is contained in an amount which is effective to achieve inhibition of proliferation and/or stimulate differentiation of the subject cancer cells. While individual needs vary, determination of optimal ranges of effective amounts of each component is within the skill in the art. Typically, the $RI_\alpha$ antisense oligonucleotide may be administered to mammals, e.g. humans, at a dose of 0.005 to 1 mg/kg/day, or an equivalent amount of the pharmaceutically acceptable salt thereof, per day of the body weight of the mammal being treated.

In addition to administering the $RI_\alpha$ antisense oligonucleotides as a raw chemical in solution, the $RI_\alpha$ antisense oligonucleotides may be administered as part of a pharmaceutical preparation containing suitable pharmaceutically acceptable carriers comprising excipients and auxiliaries which facilitate processing of the $RI_\alpha$ antisense oligonucleotide into preparations which can be used pharmaceutically.

Suitable formulations for parenteral administration include aqueous solutions of the $RI_\alpha$ antisense oligonucleotides in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The antisense oligonucleotides of the present invention may be prepared according to any of the methods that are well known to those of ordinary skill in the art. Preferably, the antisense oligonucleotides are prepared by solid phase synthesis. See, Goodchild, J., *Bioconjugate Chemistry*, 1:165–167 (1990), for a review of the chemical synthesis of oligonucleotides. Alternatively, the antisense oligonucleotides can be obtained from a number of companies which specialize in the custom synthesis of oligonucleotides.

Having now generally described this invention, the same will be understood by reference to an example which is provided herein for purposes of illustration only and is not intending to be limited unless otherwise specified. The entire text of all applications, patents and publications, if any, cited above and below are hereby incorporated by reference.

EXAMPLES

Example 1

Oligodeoxynucleotides

The 21-mer oligodeoxynucleotides used in the present studies were synthesized at Midland Certified Reagent Co. (Midland, Tex.) and had the following sequences: human $RI_\alpha$ (Sandberg, M., Tasken, K., Oyen, O., Hansson, V. & Jahnsen, T. (1987) *Biochem. Biophys. Res Commun.* 149, 939–945) antisense, 5'-GGC-GGT-ACT-GCC-AGA-CTC-CAT-3' (SEQ ID No:1); human $RII_\beta$ (Levy, F. O., Oyen, O., Sandberg, M., Tasken, K., Eskild, W., Hansson, V. & Jahnsen, T. (1988) *Mol. Endocrinol.*, 2, 1364–1373) antisense 5'-CGC-CGG-GAT-CTC-GAT-GCT-CAT-3'; human $RII_\alpha$ (Oyen, O., Myklebust, F., Scott, J. D., Hansson, V. & Jahnsen, T. (1989) *FEBS Lett*, 246, 57–64) antisense, 5'-CGG-GAT-CTG-GAT-GTG-GCT-CAT-3'; and the random sequence oligodeoxynucleotide was made of a mixture of all four nucleotides at every position.

Cell Growth Experiment

Cells grown in suspension culture in RPM1 1640 medium supplemented with 10% heat-inactivated fetal bovine serum, penicillin (50 U/ml), streptomycin (500 µg/ml), and 1 mM glutamine (Gibco, Grand Island, N.Y.) were seeded at $5 \times 10^5$ cells per dish. Oligodeoxynucleotides were added after seeding and every 48 hr thereafter. Cell counts were performed on a Coulter counter. Cells unexposed or exposed to oligodeoxynucleotides for 4 days were reseeded (day 0) at $5 \times 10^5$ cells/dish, and cells pre-exposed to the oligodeoxynucleotide were further treated with the oligomer at day 0 and day 2. cAMP analogs (kindly provided by Dr. R. K. Robins, Nucleic Acid Research Institute, Costa Mesa, Calif.) or 12-O-tetradecanoylphorbol-13-acetate (TPA) were added one time at day 0. Cell counts were performed on day 4.

Immunoprecipitation of $RI\alpha$ and $RII_{62}$ cAMP Receptor Proteins after Photoaffinity Labeling with $8\text{-}N_3\text{-}[^{32}P]cAMP$ Cell extracts were prepared at 0°–4° C. The cell pellets ($2 \times 10^6$ cells), after two washes with PBS, were suspended in 0.5 ml buffer Ten (0.1M NaCl, 5 mM $MgCl_2$, 1% Nonidet P-40, 0.5% Na deoxycholate, 2 KIU/ml bovine aprotinin, and 20 mM Tris-HCl, pH 7.4) containing proteolysis inhibitors (Tortora, G., Clair, T. & Cho-Chung, Y. S. (1990) *Proc. Natl. Acad. Sci. USA* 87, 705–708), vortex-mixed, passed through a 22-gauge needle 10 times, allowed to stand for 30 min at 4° C., and centrifuged at 750×g for 20 min; the resulting supernatants were used as cell lysates. The photoactivated incorporation of $8\text{-}N_3\text{-}[^{32}P]cAMP$ (60.0 Ci/mmol), and the immunoprecipitation using the anti-$RI_\alpha$ or anti-$RII_\beta$ antiserum (kindly provided by Dr. S. O. Dø̸skeland, University of Bergen, Bergen, Norway) and protein A Sepharose and SDS-PAGE of solubilized antigen-antibody complex followed the method previously described (Tortora, G., Clair, T. & Cho-Chung, Y. S. (1990) *Proc. Natl. Acad. Sci. USA* 87, 705–708; Ekanger, R., Sand, T. E., Ogreid, D., Christoffersen, T. & Dø̸skeland, S. O. (1985) *J. Biol. Chem.* 260, 3393–3401).

cAMP-Dependent Protein Kinase Assays

After two washes with Dulbecco's phosphate-buffered saline, cell pellets ($2 \times 10^6$ cells) were lysed in 0.5 ml of 20 mM Tris (pH 7.5), 0.1 mM sodium EDTA, 1 mM dithiothreitol, 0.1 mM pepstatin, 0.1 mM antipain, 0.1 mM chymostatin, 0.2 mM leupeptin, 0.4 mg/ml aprotinin, and 0.5 mg/ml soybean trypsin inhibitor, using 100 strokes of a Dounce homogenizer. After centrifugation (Eppendorf 5412) for 5 min, the supernatants were adjusted to 0.7 mg protein/ml and assayed (Uhler, M. D. & McKnight, G. S. (1987) *J. Biol. Chem.* 262, 15202–15207) immediately. Assays (40 µl total volume) were performed for 10 min at 30° C. and contained 200 µM ATP, $2.7 \times 10^6$ cpm $\gamma[^{32}P]ATP$, 20 mM $MgCl_2$, 100 µM Kemptide (Sigma K-1127) (Kemp, B. E., Graves, D. J., Benjamin, E. & Krebs, E.G. (1977) *J. Biol, Chem.* 252, 4888–4894), 40 mM Tris (pH 7.5), ±100 µM protein kinase inhibitor (Sigma P-3294) (Cheng, H.-C., Van Patten, S. M., Smith, A. J. & Walsh, D. A. (1985) *Biochem. J.* 231, 655–661), ±8 µM cAMP and 7 µg of cell extract. The phosphorylation of Kemptide was determined by spotting 20 µl of incubation mixture on phosphocellulose filters (Whatman, P81) and washing in phosphoric acid as described (Roskoski, R. (1983) *Methods Enzymol.* 99, 3–6). Radioactivity was measured by liquid scintillation using Econofluor-2 (NEN Research Products NEF-969).

Isolation of Total RNA and Northern Blot Analysis

The cells ($10^8$ washed twice with phosphate-buffered saline) were lysed in 4.2M guanidine isothiocyanate containing 25 mM sodium citrate (pH 7.0), 0.5% sarcosyl (N-lauroylsarcosine $Na^+$), and 0.1M β-mercaptoethanol, and the lysates were homogenized, and total cellular RNA was sedimented through a CsCl cushion (5.7M CsCl, 10 mM EDTA) as described by Chirgwin et al. (Chirgwin, J. M., Przybyla, A. E., MacDonald, R. Y. & Rutter, W. J. (1977) *Biochemistry* 18, 5284–5288). Total cellular RNA containing 20 mM 3-[N-morpholine]propane-sulfonic acid (pH 7.0), 50% formamide, and 6% formaldehyde was denatured at 65° C. for 10 min and electrophoresed through a denaturing 1.2% agarose-2.2M formaldehyde gel. The gels were then transferred to Biotrans nylon membranes (ICN Biomedicals) by the method of Thomas (Thomas, P. S. (1980) Proc. Natl. Acad. Sci. USA 77, 5201–5205) and hybridized to the following two $^{32}$P-labeled nick-translated CDNA probes: 1.5 kilobase (kb) cDNA clone containing the entire coding region for the human cAMP-dependent protein kinase type I regulatory subunit, $RI_\alpha$ (Sandberg, M., Tasken, K., Oyen, O., Hansson, V. & Jahnsen, T. (1987) Biochem. Biophys. Res. Commun. 149, 939–945) (kindly provided by Dr. T. Jahnsen, Institute of Pathology, Rikshospitalet, Oslo, Norway), and human β actin (Oncor p7000 β actin).

RESULTS

The $RI_\alpha$ antisense oligodeoxynucleotide at 15 μM concentration had immediate effects on the rate of proliferation of HL-60 cells. By 4–5 days in culture, while cells unexposed to $RI_\alpha$ antisense oligomer demonstrated an exponential rate of growth, cells exposed to the antisense oligomer exhibited a reduced growth rate and eventually stopped replicating (FIG. 1A). This inhibitory effect on cell proliferation persisted throughout the culture period. The growth inhibition was not due to cell killing; cells were over 90% viable after exposure to $RI_\alpha$ antisense oligomer (15 μM) for 7 days as assessed by flow cytometry using forward and side scatter. $RI_\alpha$ sense, $RII_\alpha$, or $RII_{62}$ antisense, or a random sequence oligodeoxynucleotide had no such growth inhibitory effect.

Figure 1B:
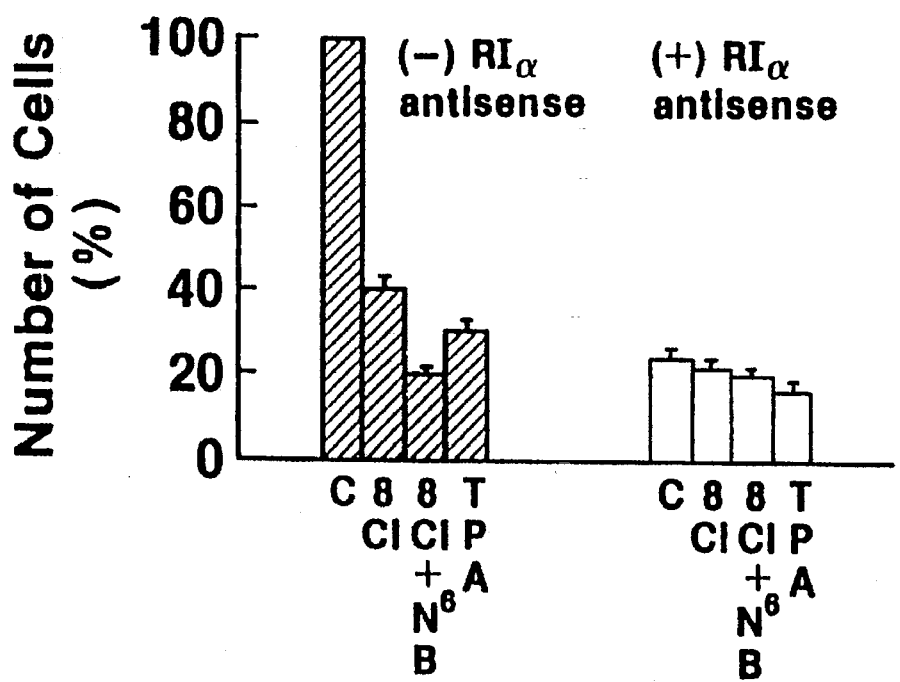
Figure 2A:
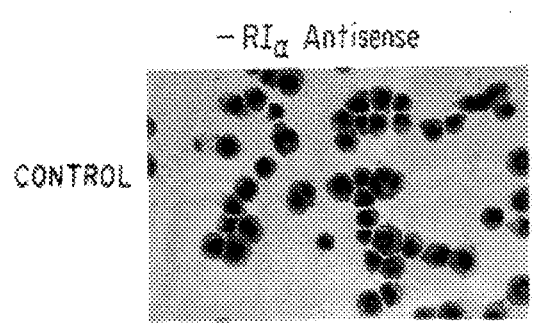
FIGS. 2A, 2B, 2C, 2D, 2E and 2F depict graphs showing the effect of $RI_\alpha$ antisense oligodeoxynucleotide (SEQ ID NO:1) on the morphologic transformation of HL-60 cells. Cells either exposed or unexposed to $RI_\alpha$ antisense oligodeoxynucleotide were treated with cAMP analogs or TPA as described in FIG. 1B. On day 4 (see FIG. 1B), cells were washed twice in Dulbecco's phosphate-buffered saline and were pelleted onto a glass slide by cytocentrifuge. The resulting cytopreparations were fixed and stained by Wright's stain.×180.
Figure 2B:
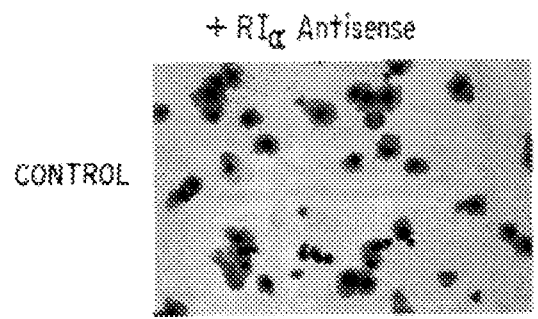
Figure 2D:
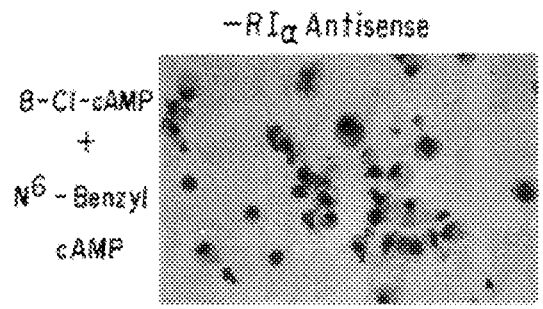
Figure 2C:
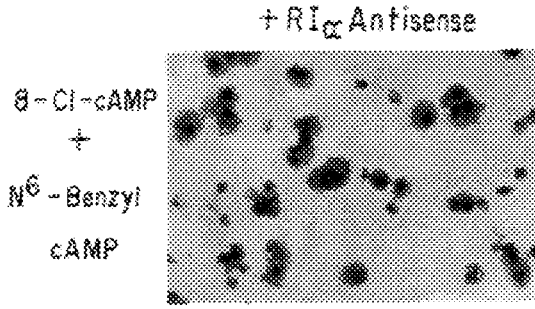
Figure 2E:
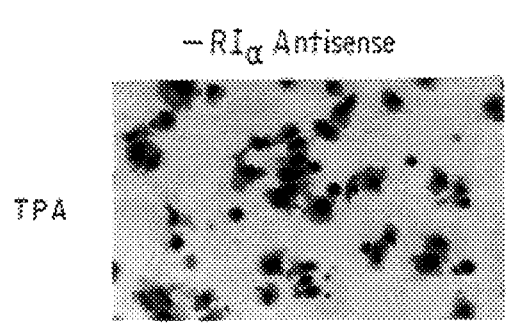
Figure 2F:
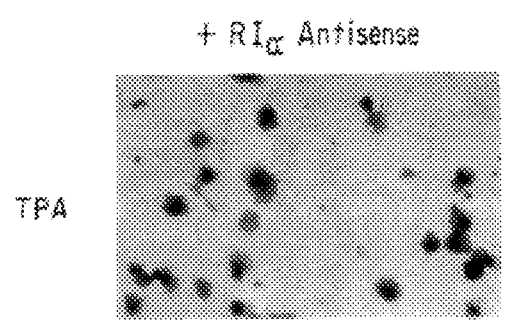

Cells unexposed or exposed to $RI_\alpha$ antisense oligodeoxynucleotide for 4 days in culture were reseeded and examined for their response to treatment with cAMP analogs or TPA. In cells unexposed to $RI_\alpha$ antisense oligodeoxynucleotide, 8-Cl-cAMP (10 μM) produced 60% growth inhibition, and 80% growth inhibition was achieved by 8-Cl-cAMP (5 μM) plus $N^6$-benzyl-cAMP (5 μM) (FIG. 1B) (Tortora, G., Tagliaferri, P., Clair, T., Colamonici, O., Neckers, L. M., Robins, R. K. & Cho-Chung, Y. S. (1988) Blood 71, 230–233), and TPA ($10^{-8}$M) exhibited 60% growth inhibition (FIG. 1B). In contrast, cells exposed to antisense oligodeoxynucleotide exhibited retarded growth (25% the rate of growth of cells unexposed to the antisense oligomer) and neither cAMP analogs nor TPA brought about further retardation of growth (FIG. 1B).

HL-60 cells undergo a monocytic differentiation upon treatment with site-selective cAMP analogs. Cells either unexposed or exposed to $RI_\alpha$ antisense oligodeoxynucleotide were examined for their morphology before and after treatment with cAMP analogs. As shown in FIG. 2, in cells unexposed to $RI_\alpha$ antisense oligomer, 8-Cl-cAMP plus $N^6$-benzyl-cAMP induced a monocytic morphologic change characterized by a decrease in nuclear-to-cytoplasm ratio, abundant ruffled and vacuolated cytoplasm, and loss of nucleoli. Strikingly, the same morphologic change was induced when cells were exposed to $RI_\alpha$ antisense oligodeoxynucleotide (FIG. 2). Moreover, the morphologic changes induced by antisense oligomer were indistinguishable from that induced by TPA (FIG. 2).

Figure 3A:
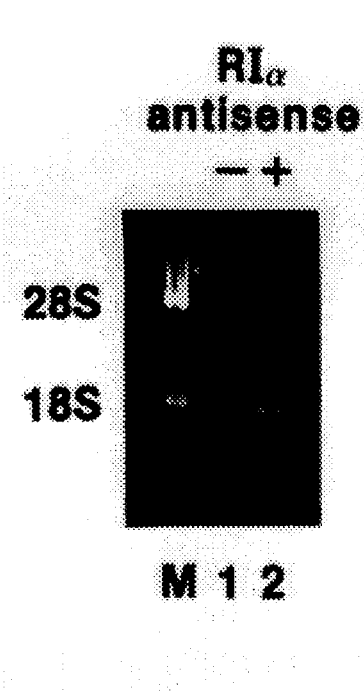
FIGS. 3A and 3B depict Northern blots showing decreased $RI_\alpha$ mRNA expression in HL-60 leukemic cells exposed to $RI_\alpha$ antisense oligodeoxynucleotide (SEQ ID NO:1). Cells were either exposed or unexposed to $RI_\alpha$ antisense oligodeoxynucleotide (15 µM) for 8 hr. Isolation of total RNA and Northern blot analysis followed the methods described in the Examples. A, ethidium bromide staining of RNA; M, markers of ribosomal RNAs; lanes 1, 2, cells unexposed or exposed to $RI_\alpha$ antisense oligomer. B, Northern blot analysis; the same nitrocellulose filter was hybridized to both $RI_\alpha$ and actin probes in sequential manner. Lanes 1, 2, cells unexposed or exposed to $RI_\alpha$ antisense oligomer.
Figure 3B:
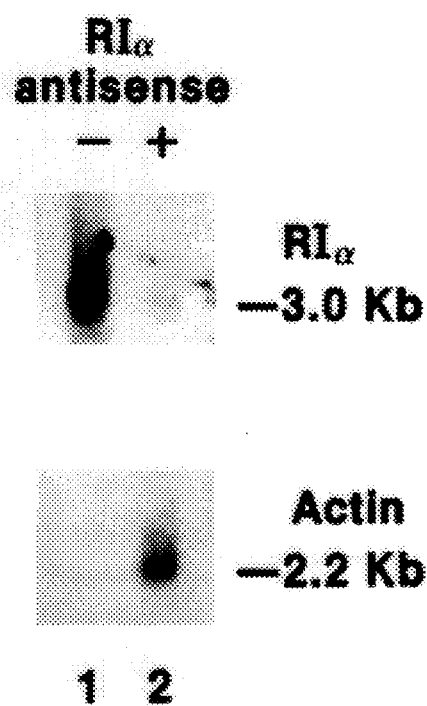
Figure 5A:
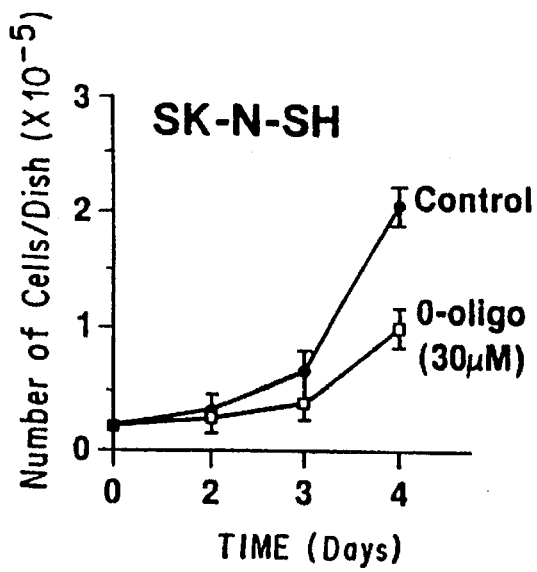
FIGS. 5A, 5B, 5C and 5D depict graphs showing the growth inhibition of human cancer cell lines by $RI_\alpha$ antisense oligodeoxynucleotide having SEQ ID No: 1 (O-oligo and S-oligo derivatives), compared to controls. Cell lines: SK-N-SH, neuroblastoma; LS-174T, colon carcinoma; MCF-7, breast carcinoma; TMK-1, gastric carcinoma. $E_2$, estradiol-17β.
Figure 5B:
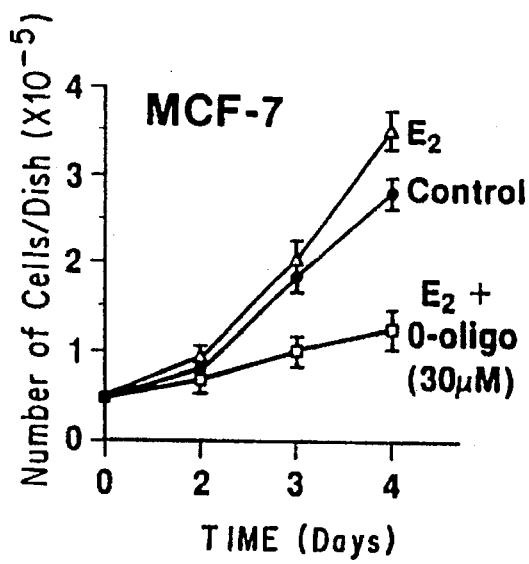
Figure 5C:
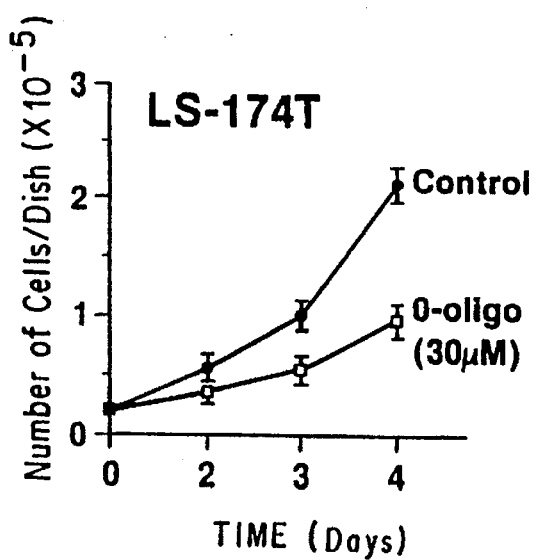
Figure 5D:
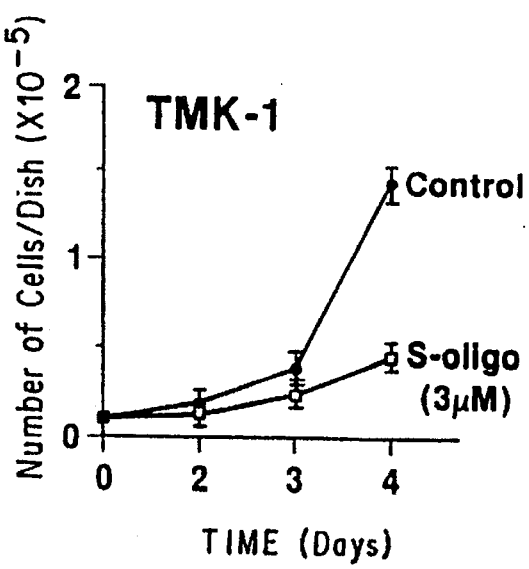

To provide more evidence that the growth inhibition and monocytic differentiation induced in HL-60 cells exposed to the $RI_\alpha$ antisense oligodeoxynucleotide were due to an intracellular effect of the oligomer, the $RI_\alpha$ mRNA level was determined. As shown in FIG. 3, 3.0 kb $RI_\alpha$ mRNA (Sandberg, M., Tasken, K., Oyen, O., Hansson, V. & Jahnsen, T. (1987) Biochem. Biophys. Res. Commun. 149, 939–945) was virtually undetectable in cells exposed for 8 hr to $RI_\alpha$ antisense oligodeoxynucleotide (FIG. 3B, lane 2), and the decrease in $RI_\alpha$ mRNA was not due to a lower amount of total RNA as shown by the ethidium bromide staining (compare lane 2 with lane 1 of FIG. 3A). Conversely, an enhanced level of actin mRNA was detected in cells exposed to $RI_\alpha$ antisense oligomer (FIG. 3B). Whether the increase in actin mRNA level represents changes in cytoskeletal structure is not known.

The levels of cAMP receptor proteins in these cells was then determined by immunoprecipitation using anti-$RI_\alpha$ and anti-$RII_{62}$ antisera (Tortora, G., Clair, T. & Cho-Chung, Y. S. (1990) Proc. Natl. Acad. Sci. USA 87, 705–708; Ekanger, R., Sand, T. E., Ogreid, D., Christoffersen, T. & Døskeland, S. O. (1985) J. Biol. Chem. 260, 3393–3401) after photoaffinity labeling of these receptor proteins with 8-$N_3$-[$^{32}$P]cAMP. In control cells, treatment with 8-Cl-cAMP plus $N^6$-benzyl-cAMP brought about a 70% reduction in $RI_\alpha$ with a 3-fold increase in $RII_\beta$, resulting in a 10-fold increase in the ratio of $RII_\beta/RI_\alpha$ (FIG. 4) (Cho-Chung, Y. S. (1989) J. Natl. Cancer Inst. 81, 982–987). Exposure of these cells to $RI_\alpha$ antisense oligodeoxynucleotide for 4 days brought about marked changes in both and $RI_\alpha$ and $RII_{62}$ levels; an 80% reduction in $RI_\alpha$ with a 5-fold increase in $RII_\beta$ resulted in a 25-fold increase in the ratio of $RII_\beta/RI_\alpha$ compared with that in control cells (FIG. 4). Since growth inhibition and differentiation were appreciable after 3–4 days of exposure to $RI_\alpha$ antisense oligomer, the changing levels of $RI_\alpha$ and $RII_{62}$ proteins appears to be an early event necessary for commitment to differentiation.

Data in FIG. 4 showed that suppression of $RI_\alpha$ by the antisense oligodeoxynucleotide brought about a compensatory increase in $RII_{62}$ level. Such coordinated expression of RI and RII without changes in the amount of C subunit has been shown previously (Hofman, F., Bechtel, P. J. & Krebs, E. G. (1977) J. Biol. Chem. 252, 1441–1447; Otten, A. D. & Mcknight, G. S. (1989) J. Biol. Chem. 264, 20255–20260). The increase in $RII_{62}$ may be responsible for the differentiation induced in these cells after exposure to $RI_\alpha$ antisense oligodeoxynucleotide. The increase in $RII_\beta$ mRNA or $RII_{62}$ protein level has been correlated with cAMP analog-induced differentiation in K-562 chronic myelocytic leukemic cells (Tortora, G., Clair, T., Katsaros, D., Ally, S., Colamonici, O., Neckers, L. M., Tagliaferri, P., Jahnsen, T., Robins, R. K. & Cho-Chung, Y. S. (1989) Proc. Natl. Acad. Sci. USA 86, 2849–2852) and in erythroid differentiation of Friend erythrocytic leukemic cells (Schwartz, D. A. & Rubin, C. S. (1985) J. Biol. Chem. 260, 6296–6303). In a recent report (Tortora, G., Clair, T. & Cho-Chung, Y. S. (1990) Proc. Natl. Acad. Sci. USA 87, 705–708), we have provided direct evidence that $RII_{62}$ is essential for the cAMP-induced differentiation in HL-60 cells. HL-60 cells that were exposed to $RII_{62}$ antisense oligodeoxynucleotide became refractory to treatment with cAMP analogs and continued to grow.

The essential role of $RII_{62}$ in differentiation of HL-60 cells was further demonstrated when these cells were exposed to both $RI_\alpha$ and $RII_{62}$ antisense oligodeoxynucleotides simultaneously. As shown in Table 1, $RI_\alpha$ antisense oligodeoxynucleotide (SEQ ID NO:1) induced a marked increase in the expression of monocytic surface antigens [Leu 15 (Landay, A., Gartland, L. & Clement, L. T. (1983) J. Immunol. 131, 2757–2761) and Leu M3 (Dimitriu-Bona, A., Burmester, G. R., Waters, S. J. & Winchester, R. J. (1983) J. Immunol. 130, 145–152)] along with a decrease in markers related to the immature myelogenous cells [My9 (Talle, M. A., Rao, P. E., Westberg, E., Allegar, N., Makowski, M., Mittler, R. S. & Goldstein, G. (1983) Cell. Immunol. 78, 83.; Todd, R. F. III, Griffin, J. D., Ritz, J., Nadler, L. M. Abrams, T. & Schlossman, S. F. (1981) Leuk.

Res. 5, 491)]. These changes in surface marker expression were abolished when cells were exposed simultaneously to both $RI_\alpha$ and $RII_\beta$ antisense oligodeoxynucleotides (Table 1). $RII_{60}$ cAMP receptor was not detected in HL-60 cells (Cho-Chung, Y. S., Clair, T., Tagliaferri, P., Ally, S., Katsaros, D., Tortora, G., Neckers, L., Avery, T. L., Crabtree, G. W. & Robins, R. K. (1989) *Cancer Invest.* 7(2), 161-177), and $RII_{60}$ antisense oligodeoxynucleotide showed no interference with the effects of $RI_\alpha$ antisense oligomer (Table 1).

Cells exposed to both $RI_\alpha$ and $RII_{62}$ antisense oligodeoxynucleotides were neither growth inhibited nor differentiated regardless of cAMP analog treatment. We interpret these results to reflect the blockage of cAMP-dependent growth regulatory pathway. Cells under these conditions are no longer cAMP-dependent but survive and proliferate probably through an alternate pathway. Thus, suppression of both $RI_\alpha$ and $RII_{62}$ gene expression led to an abnormal cellular growth regulation similar to that in mutant cell lines (Gottesman, M. M. (1980) *Cell* 22, 329-330), those that contain either deficient or defective regulatory subunits of cAMP-dependent protein kinase and are no longer sensitive to cAMP stimulus.

Our results demonstrated that cAMP transduces signals for dual controls, either positive or negative, on cell proliferation, depending on the availability of $RI_\alpha$ or $RII_{62}$ receptor proteins. The $RI_\alpha$ antisense oligodeoxynucleotide which brought about suppression of $RI_\alpha$ along with enhancement of $RII_\beta$ expression led to terminal differentiation of HL-60 leukemia with no sign of cytotoxicity.

It is unlikely that free C subunit increase in cells exposed to $RI_\alpha$ antisense oligodeoxynucleotide was responsible for the differentiation, because cells exposed to $RII_\beta$ antisense or both $RI_\alpha$ and $RII_\beta$ antisense oligodeoxynucleotides, conditions which also would produce free C subunit, continued to grow and became refractory to cAMP stimulus. In order to directly verify this we measured phosphotransferase activity in cells that are exposed or unexposed to the antisense oligodeoxynucleotides using kemptide (Kemp, B. E., Graves, D. J., Benjamin, E. & Krebs, E. G. (1977) *J. Biol. Chem.* 252, 4888-4894) as a substrate in the presence and absence of a saturating concentration of cAMP and in the presence and absence of the heat-stable protein kinase inhibitor (Cheng, H.-C., Van Patten, S. M., Smith, A. J. & Walsh, D. A. (1985) *Biochem. J.* 231, 655-661). This method of assay gives accurate determination of the relative levels of dissociated C and total C activity. Cell extracts from untreated HL-60 cells exhibited a very low level of dissociated C and were stimulated 36-fold by cAMP (Table 2). This cAMP-stimulated activity was almost completely inhibited by the heat-stable protein kinase inhibitor (Table 2), indicating that the total C activity measured was cAMP-dependent protein kinase. In cells exposed to $RI_\alpha$ antisense, $RII_\beta$ antisense, or $RI_\alpha$ and $RII_\beta$ antisense oligodeoxynucleotide, the free C activity was not increased as compared to unexposed control cells, although there was a small difference in the total cAMP-stimulated activity (Table 2). These results provide direct evidence that free catalytic subunit is not responsible for the differentiation observed in HL-60 cells.

Over expression of $RI_\alpha$ cAMP receptor protein has also been found in the majority of human breast and colon primary carcinomas examined (Bradbury, A. W., Miller, W. R., Clair, T., Yokozaki, H. & Cho-Chung, Y. S. (1990) *Proc. Am. Assoc. Cancer Res.* 31, 172), suggesting an important in vivo role of cAMP receptor in tumor growth as well. However, the precise role of $RI_\alpha$ in cell proliferation is not known at present. $RI_\alpha$ may suppress $RII_\beta$ production by titrating out C subunit, or it may be a transducer of mitogenic signals leading to cell proliferation. Our results demonstrate that $RI_\alpha$ antisense oligodeoxynucleotide provides a useful genetic tool for studies on the role of cAMP receptor proteins in cell proliferation and differentiation, and contribute to a new approach in the control of malignancy.

TABLE 1

Modulation of differentiation markers in HL-60 cells by $RI_\alpha$ antisense oligodeoxynucleotide

| Treatment | Surface Makers | | |
|---|---|---|---|
| | Leu15 | LeuM3 | My9 |
| Control | 10 | 2 | 100 |
| $RI_\alpha$ antisense | 80 | 98 | 80 |
| $RI_\alpha$ antisense + $RII_\beta$ antisense | 11 | 2 | 100 |
| $RII_\beta$ antisense | 13 | 3 | 100 |
| $RI_\alpha$ antisense + $RII_\alpha$ antisense | 85 | 100 | 80 |

Surface antigen analysis was performed by flow cytometry using monoclonal antibodies reactive with either monocytic or myeloid cells. The monoclonal antibodies used were Leu 15, Leu M3, and My9. $2\times10^4$ cells were analyzed for each sample, and cell gating was performed using forward and side scatter. The numbers represent % positive and represent the average values of three experiments.

TABLE 2

Protein kinase activity in HL-60 cells

| Treatment | Activity − cAMP | Relative to control | Activity + cAMP | Relative to control | Stimulation (fold) |
|---|---|---|---|---|---|
| −PKI | | | | | |
| Control | 23.0 ± 6.6 | 1.0 | 837 ± 87 | 1.0 | 36 |
| $RI_\alpha$ antisense | 22.9 ± 5.4 | 1.0 | 944 ± 18 | 1.1 | 41 |
| $RII_\beta$ antisense | 22.8 ± 8.1 | 1.0 | 1,028 ± 154 | 1.2 | 45 |
| $RI_\alpha$ and $RII_\beta$ antisense | 24.3 ± 7.0 | 1.1 | 802 ± 36 | 1.0 | 33 |
| +PKI | | | | | |
| Control | 17.5 ± 8.7 | 1.0 | 37.0 ± 8.4 | 1.0 | 2.1 |
| $RI_\alpha$ antisense | 25.0 ± 8.8 | 1.4 | 22.6 ± 8.8 | 0.6 | 0.9 |
| $RII_\beta$ antisense | 24.0 ± 2.6 | 1.4 | 24.8 ± 3.9 | 0.7 | 1.0 |
| $RI_\alpha$ and $RII_\beta$ antisense | 19.0 ± 5.9 | 1.1 | 19.1 ± 8.2 | 0.5 | 1.0 |

Cells were exposed to each of 15 μM concentrations of $RI_\alpha$, $RII_\beta$, or $RI_\alpha$ and $RII_\beta$ antisense oligodeoxynucleotide for 4 days as shown in FIG. 1A. The data represent an average±SD of duplicate determinations of three identical experiments.

*Picomoles phosphate transferred to Kemptide per min/mg protein.

Example 2

Next, the $RI_\alpha$ antisense oligonucleotide having SEQ ID NO:1 was administered to mice having an experimental tumor. A pellet of $RI_\alpha$ antisense oligonucleotide (25 mg/Kg) and cholesterol (1000 mg/Kg) was implanted s.c. in the left flank of athymic mice which had been injected in the right flank with LS-174T human colon cancer cells ($2 \times 10^6$ cells) suspended in phosphate-buffered saline. Tumor measurements and mouse weights were recorded on the initial day of treatment (staging day), and at the end of treatment (staging day +5). The mean tumor weight change (Δ), was based on length and width measurements in millimeters. After a few days, the tumor growth was inhibited when compared to control cells (see Table 3). No change in body weight was noted in the control and treated animals.

TABLE 3

Effect of $RI_\alpha$ antisense oligodeoxynucleotide s.c. pellet on the growth of LS-174T human colon carcinoma in athymic mice

| | Initial mean[c] tumor wt (mg) | Final mean[d] tumor wt (mg) | % ΔT/ΔC[e] |
|---|---|---|---|
| Treatment[a] s.c. pellet implanted | | | |
| Control | 25 | 450 | — |
| $RI_\alpha$ antisense (0.5 mg) | 25 | 230 | 48 |
| 8-Cl cAMP (1 mg)[b] + $N^6$benzyl cAMP (1 mg) | 34 | 250 | 51 |

[a] 20 mg pellet lyophilized consisting of indicated doses of $RI_\alpha$ antisense or cAMP analogs plus supplement doses of cholesterol.
[b] The growth inhibitory effect of these cAMP analogs correlate with decrease in $RI_\alpha$ (Natl. Cancer Inst. 81 982 (1989)) and is shown here for comparison.
[c] Mean tumor weight per group (4 mice) on staging day.
[d] Mean tumor weight per group on staging day +5.
[e] % of change in test tumor weight (ΔT)/change in control tumor weight (ΔC).

Figure 6A:
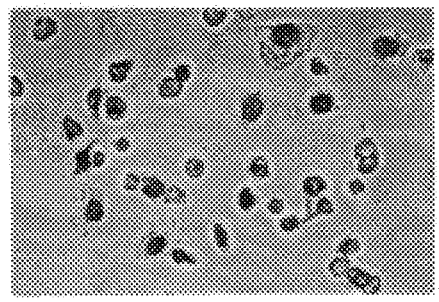
FIGS. 6A, 6B, and 6C depict the change in morphology of SK-N-SH human neuroblastoma cells exposed to $RI_\alpha$ antisense oligodeoxynucleotide having SEQ ID No: 1.
Figure 6B:
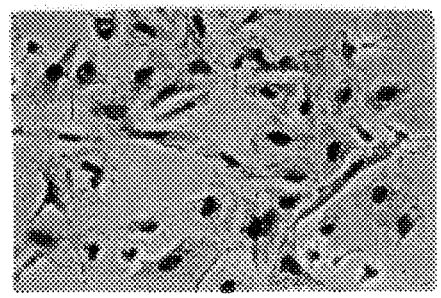
Figure 6C:
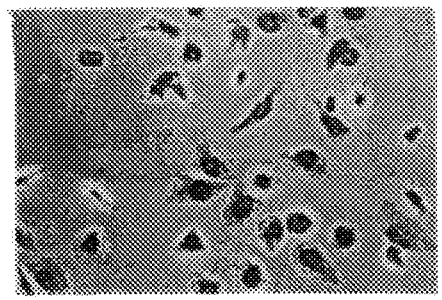

In other in vitro experiments, the $RI_\alpha$ antisense oligonucleotide having SEQ ID NO: 1 was added to dishes containing neuroblastoma, colon carcinoma, breast carcinoma and gastric carcinoma cells. As shown in FIG. 5, the $RI_\alpha$ antisense oligonucleotide having SEQ ID No: 1 inhibited proliferation of all cancer cell types when compared to control cells. Moreover, the $RI_\alpha$ antisense oligonucleotide having SEQ ID No: 1 caused differentiation of the human neuroblastoma cells (see FIG. 6).

Example 3

Next, the effect of O-oligo and S-oligo $RI_\alpha$ antisense oligonucleotides on the growth of LS-174T human colon carcinoma in athymic mice was compared.

Materials and Methods

We synthesized [Milligen Biosearch 8700 DNA synthesizer (Bedford, Mass.)] the 21-mer antisense oligodeoxynucleotides and their phosphorothioate analogs complementary to the human $RI_\alpha$, human $RII_\beta$ mRNA transcripts starting from the first codon, and mismatched sequence (random) oligomers of identical size. The oligomers had the following sequences: $RI_\alpha$ antisense, 5'-GGC-GGT-ACT-GCC-AGA-CTC-CAT-3'(SEQ ID NO:1); $RII_\alpha$ antisense, 5'-CGC-CGG-GAT-CTC-GAT-GCT-CAT-3'; and random oligo, 5'-CGA-TCG-ATC-GAT-CGA-TCG-TAC-3'.

LS-174T human colon carcinoma cells ($2 \times 10^6$) were injected s.c. in athymic mice, and the antisense oligodeoxynucleotides in the form of either a cholesterol pellet or 50% sesame oil emulsion were administered s.c. 1 week later when mean tumor sizes usually were 25–50 mg. Tumor volume was based on length and width measurements and calculated by the formula $4/3\ \pi r^3$, where r=(length+width)/4.

Results and Discussion

Figure 7B:
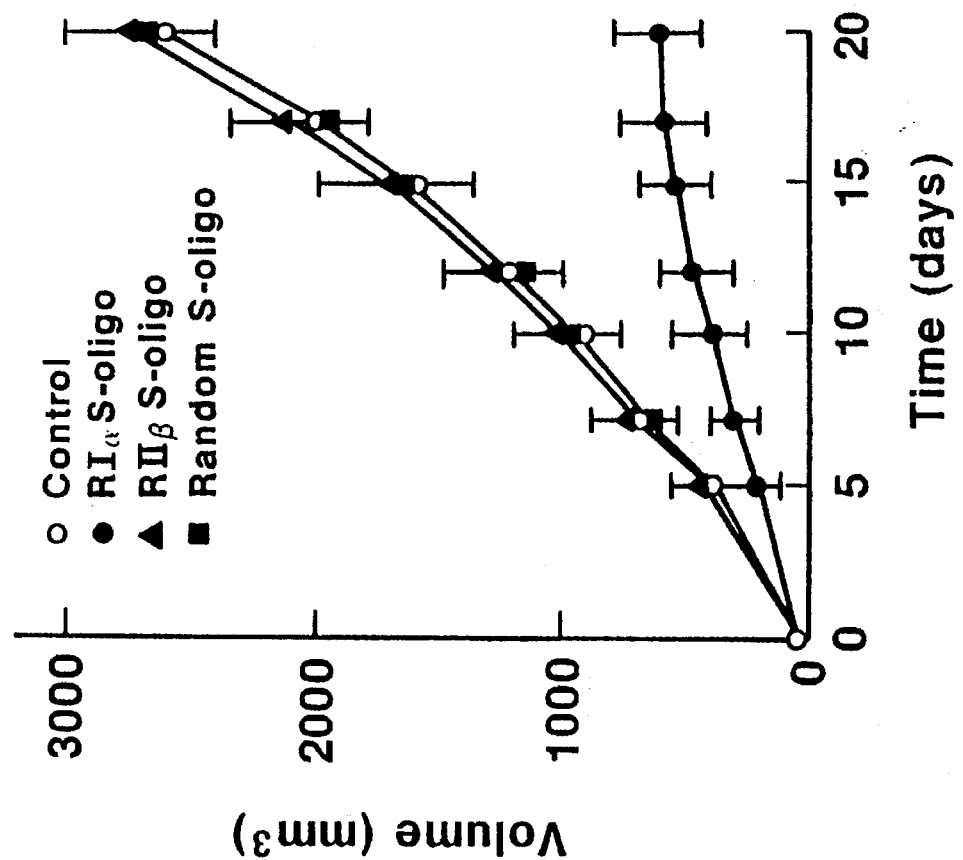
FIGS. 7A and 7B depict graphs showing that $RI_\alpha$ antisense oligodeoxynucleotide and its phosphorothioate analog (SEQ ID NO:1) inhibit the in vivo growth of LS-174T human colon carcinoma in athymic mice.
Figure 7A:
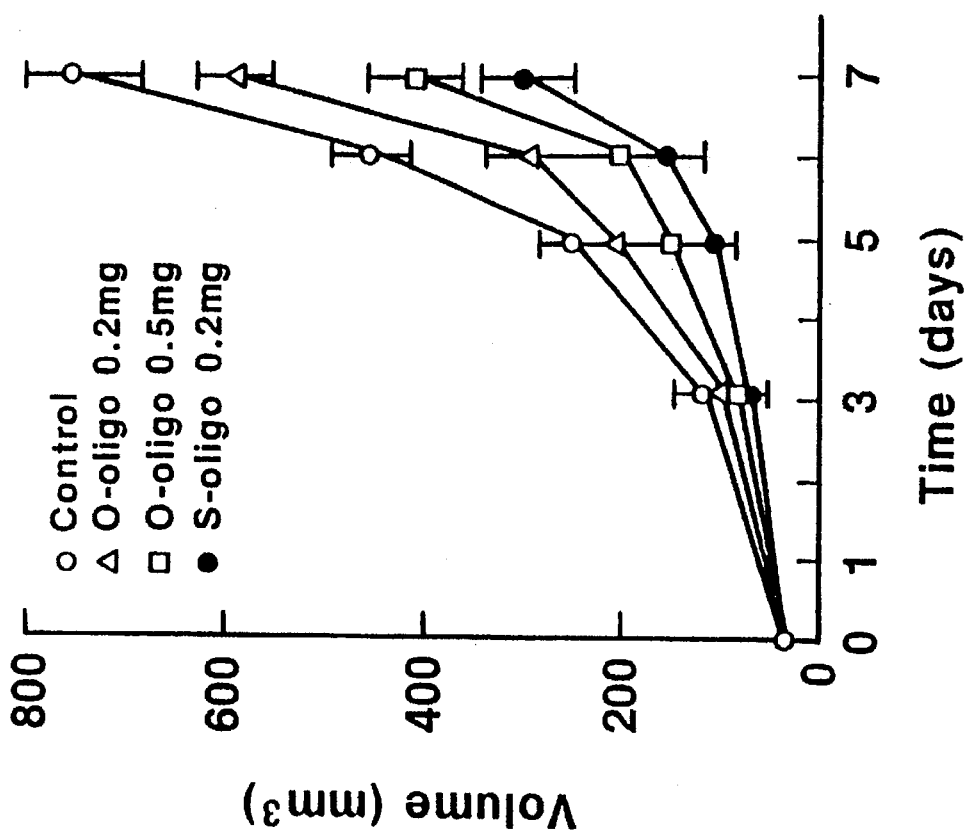

FIG. 7 shows the dose- and time-dependent effect of an $RI_\alpha$ antisense oligodeoxynucleotide (O-oligo) at 0.2 and 0.5 mg doses in cholesterol pellets administered s.c. one time (at zero time); it brought about 20 and 46% growth inhibition, respectively, in 7 days when compared with control (untreated) tumors (FIG. 7A). Strikingly, the $RI_\alpha$ antisense phosphorothioate analog (S-oligo) at a 0.2 mg dose (cholesterol pellet, s.c.) gave a 60% growth inhibition at day 7, exhibiting a 3-fold greater potency than the O-oligo antisense (FIG. 7A). The growth inhibitory effect of $RI_\alpha$ antisense S-oligo was even greater when animals were treated for a longer period. The $RI_\alpha$ antisense S-oligo at a 0.3 mg dose in a cholesterol pellet, 2 times/week s.c. implantation for 3 weeks, resulted in a 80% growth inhibition; the tumor growth almost stopped after 2 weeks of treatment (FIG. 7B). $RI_\alpha$ antisense O-oligo or S-oligo administered s.c. as 50% sesame oil emulsion gave similar results. $RI_\alpha$ antisense S-oligo brought about no apparent toxicity in animals; no body weight loss or other toxic symptoms were observed during the 3 weeks of treatment.

The growth inhibitory effect brought about by $RI_\alpha$ antisense S-oligo was the specific effect of the oligomer: $RII_{\beta2}$ antisense or random (mismatched sequence) S-oligos of the identical size as the $RI_\alpha$ antisense oligomer had no effect on the tumor growth (FIG. 7B).

To provide more evidence that the growth inhibition observed in colon carcinomas in athymic mice treated with $RI_\alpha$ antisense oligodeoxynucleotide was due to an intracellular effect of the oligomer, the levels of $RI_\alpha$ and $RII_{\beta2}$ cAMP receptor proteins in these tumors were determined. $RI_\alpha$ levels were determined by immunoblotting (Ally, S., Proc. Natl. Acad. Sci. USA 85:6319–6322 (1988)) using monoclonal antibody against human $RI_\alpha$ (kindly provided by Drs. T. Lea, University of Oslo, Oslo, Norway, and S. O. Døskeland, University of Bergen, Bergen, Norway), and $RII_{\beta2}$ was measured by immunoprecipitation (Tortora, G., et al., Proc. Natl. Acad. Sci. USA 87:705–708 (1990)) with anti-$RII_{\beta2}$ antiserum (kindly provided by Dr. S. O. Døskeland) after photoaffinity labeling of $RII_{\beta2}$ with [$^{32}$P] 8-$N_3$-cAMP. As shown in Table 4, $RI_\alpha$ antisense S-oligomer treatment brought about a marked reduction (80% decrease) of $RI_\alpha$ level in tumors as compared with that in untreated control tumors. This suppression of $RI_\alpha$ expression by $RI_\alpha$ antisense S-oligomer brought about a 2-fold increase in RII$_{62}$ level (Table 4). Such coordinated expression of RI$_\alpha$ and RII$_\beta$ without changes in the amount of catalytic subunit of protein kinase has been shown in HL-60 leukemia cells that demonstrated growth inhibition and differentiation upon exposure to RI$_\alpha$ antisense oligodeoxynucleotide. On the other hand, a 50% increase in RI$_\alpha$ level along with 80% suppression in RII$_\beta$ level was observed in tumors after treatment with RII$_\beta$ antisense S-oligomer (Table 4) which had no effect on tumor growth (FIG. 7). Random (mismatched sequence) S-oligomer which had no effect on tumor growth (FIG. 7) also showed no effect on RI$_\alpha$ levels (Table 4). Thus, reduction in RI$_\alpha$ expression appears to trigger a decrease or halt in tumor growth upon treatment with RI$_\alpha$ antisense oligomer. Our results demonstrated that cAMP transduces signals for dual control, either positive or negative, on cell proliferation, depending on the availability of RI$_\alpha$ or RII$_\beta$ receptor proteins. The RI$_\alpha$ antisense oligodeoxynucleotide, which suppressed RI$_\alpha$ and enhanced RII$_{62}$ expression, led to inhibition of in vivo growth of solid colon carcinoma in athymic mice with no symptoms of toxicity in animals. The phosphorothioate analog (S-oligo) of RI$_\alpha$ antisense oligomer exhibited a greater potency than the antisense of unmodified oligodeoxynucleotide (O-oligo). It has been shown that S-oligos, as compared with O-oligos, more readily enter cells, are more resistant to endonucleases, and yet exhibit high efficacy in hybridization with target mRNAs or DNAs (Stein, C. A., et al., In: J. S. Cohen (ed.), *Oligodeoxynucleotides: Antisense Inhibitors of Gene Expression*, pp. 97–117. Boca Raton, Fla., CRC Press, Inc. (1989)).

These results demonstrate here for the first time the striking in vivo effect of antisense oligodeoxynucleotide in the suppression of malignancy. The depletion of RI$_\alpha$, the type I regulatory subunit of cAMP-dependent protein kinase, by means of an antisense oligodeoxynucleotide, especially with its phosphorothioate analog, leads to a successful halt of tumor growth in vivo with no symptoms of toxicity, suggesting great potential of this antisense oligodeoxynucleotide for clinical application.

TABLE 4

Suppression of RI$_\alpha$ cAMP Receptor Expression by RI$_\alpha$ Antisense Oligodeoxynucleotide (S-oligo) Results in Compensatory Increase in RII$_\beta$ Receptor

| | Relative Levels | |
|---|---|---|
| Treatment | RI$_\alpha$ | RII$_\beta$ |
| None | 1.0 ± 0.1 | 1.0 ± 0.1 |
| RI$_\alpha$ antisense S-oligo | 0.2 ± 0.03 | 2.0 ± 0.2 |
| RII$_\beta$ antisense S-oligo | 1.5 ± 0.2 | 0.2 ± 0.02 |
| Random S-oligo | 1.0 ± 0.1 | 1.0 ± 0.1 |

Treatment with S-oligos as indicated were the same as that in FIG. 7B. At the end of the experiment (3 weeks), tumor extracts were prepared as previously described (Ally, S. et al., *Cancer Res.* 49:5650–5655 (1980)) and immunoblotting and immunoprecipitation of RI$_\alpha$ and RII$_\beta$, respectively, were performed as previously described by Ally, S., et al., *Proc. Natl. Acad. Sci. USA* 85:6319–6322 (1988) and Tortora, G., et al., *Proc. Natl. Acad. Sci. USA* 87:705–708 (1990). Data are from quantification by densitometric scanning of autoradiograms. Data are expressed relative to levels in control tumors (no treatment), which are set to equal to one as an arbitrary unit.

Data represent an average±S.D. of 7 tumors.

In the following sequence listing, Seq ID No: 1 represents an antisense sequence corresponding to the first 7 N-terminal codons for RI$_\alpha$. Seq ID No: 2 represents an antisense sequence corresponding to the $8^{th}$–$13^{th}$ codon for RI$_\alpha$. Seq ID No: 3 represents an antisense sequence corresponding to the $14^{th}$–$20^{th}$ codon for RI$_\alpha$. Seq ID No: 4 represents an antisense sequence corresponding to the $94^{th}$–$100^{th}$ codon for RI$_\alpha$. Seq ID No: 5 represents an antisense sequence corresponding to the $1^{st}$–$100^{th}$ codon for RI$_\alpha$. Seq ID No: 6 represents the sense sequence corresponding to the $1^{st}$–$100^{th}$ codon for RI$_\alpha$.

---

I claim:

1. A method for reducing growth of cancer cells susceptible to growth reduction in a mammal comprising administering subcutaneously or parenterally to a mammal in need of such treatment a cancer cell growth-reducing amount of at least one 15- to 30-mer antisense 5' to 3'-oligonucleotide which is complementary to a region in the nucleic acid encoding the first 100 N-terminal amino acids of $RI_\alpha$, which nucleic acid consists of the nucleotide sequence shown as SEQ. ID No:6.

2. The method of claim 1, wherein said antisense 5' to 3'-oligonucleotide is a 5' to 3'-oligodeoxynucleotide.

3. The method of claim 1, wherein said antisense 5' to 3'-oligonucleotide is a 21-mer consisting of the nucleotide sequence shown as SEQ. ID No:1.

4. The method of claim 1, wherein said antisense 5' to 3'-oligonucleotide is an 18-mer consisting of the nucleotide sequence shown as SEQ. ID No:2.

5. The method of claim 1, wherein said antisense 5' to 3'-oligonucleotide is a 21-mer consisting of the nucleotide sequence shown as SEQ. ID No:3.

6. The method of claim 1, wherein said antisense 5' to 3'-oligonucleotide is a 21-mer consisting of the nucleotide sequence shown as SEQ. ID No:4.

7. The method of claim 1, wherein said cancer is selected from the group consisting of leukemia, melanoma, sarcoma, and carcinoma.

8. The method of claim 1, wherein said antisense 5' to 3'-oligonucleotide is administered as part of a pharmaceutical composition comprising a pharmaceutically acceptable carrier.

9. The method of claim 1, wherein said antisense 5' to 3'-oligonucleotide is a 5' to 3' O-oligodeoxynucleotide.

10. The method of claim 1, wherein said antisense 5' to 3'-oligonucleotide is a 5' to 3'-oligodeoxynucleotide-phosphorothioate.

* * * * *

UNITED STATES PATENT AND TRADEMARK OFFICE
CERTIFICATE OF CORRECTION

PATENT NO. : 5,627,158

DATED : May 6, 1997

INVENTOR(S) : Yoon S. Cho-Chung

It is certified that error appears in the above-identified patent and that said Letters Patent is hereby corrected as shown below:

On the title page:

item [54], line 3, delete "CAMP" insert therein --cAMP--.

In column 1, line 3, delete "CAMP" insert therein --cAMP--.

In column 2, line 38, delete "selection" insert therein --selective--.

In column 2, line 38, delete "$RII_{62}$" insert therein --$RII_\beta$--.

In column 2, line 46, delete "$RII_{62}$" insert therein --$RII_\beta$--.

In column 2, line 50, delete "$RII_{62}$" insert therein --$RII_\beta$--.

In column 4, line 21, delete "$RII_{62}$" insert therein --$RII_\beta$--.

In column 4, line 28, delete "$RII_{62}$" insert therein --$RII_\beta$--.

In column 4, line 31, delete "$RII_{62}$" insert therein --$RII_\beta$--.

In column 5, line 25, delete "$RI_{60}$" insert therein --$RI_\alpha$--.

In column 8, line 3, delete "$RII_{62}$" insert therein --$RII_\beta$--.

In column 9, line 26, delete "$RII_{62}$" insert therein --$RII_\beta$--.

In column 10, line 10, delete "$RII_{62}$" insert therein --$RII_\beta$--.

In column 10, line 21, delete "$RII_{62}$" insert therein --$RII_\beta$--.

In column 10, line 26, delete "$RII_{62}$" insert therein --$RII_\beta$--.

In column 10, line 31, delete "$RII_{62}$" insert therein --$RII_\beta$--.

In column 10, line 36, delete "$RII_{62}$" insert therein --$RII_\beta$--.

UNITED STATES PATENT AND TRADEMARK OFFICE
CERTIFICATE OF CORRECTION

PATENT NO. : 5,627,158

DATED : May 6, 1997

INVENTOR(S) : Yoon S. Cho-Chung

It is certified that error appears in the above-identified patent and that said Letters Patent is hereby corrected as shown below:

In column 10, line 38, delete "$RII_{62}$" insert therein --$RII_{\beta}$--.

In column 10, line 49, delete "$RII_{62}$" insert therein --$RII_{\beta}$--.

In column 10, line 51, delete "$RII_{62}$" insert therein --$RII_{\beta}$--.

In column 10, line 53, delete "$RII_{62}$" insert therein --$RII_{\beta}$--.

In column 10, line 55, delete "$RII_{62}$" insert therein --$RII_{\beta}$--.

In column 11, line 4, delete "$RII_{60}$" insert therein --$RII_{\alpha}$--.

In column 11, line 8, delete "$RII_{60}$" insert therein --$RII_{\alpha}$--.

In column 11, line 11, delete "$RII_{62}$" insert therein --$RII_{\beta}$--.

In column 11, line 18, delete "$RII_{62}$" insert therein --$RII_{\beta}$--.

In column 11, line 26, delete "$RII_{62}$" insert therein --$RII_{\beta}$--.

UNITED STATES PATENT AND TRADEMARK OFFICE
CERTIFICATE OF CORRECTION

PATENT NO. : 5,627,158
DATED : May 6, 1997
INVENTOR(S) : Yoon S. Cho-Chung

It is certified that error appears in the above-identified patent and that said Letters Patent is hereby corrected as shown below:

In column 14, line 6, delete "$RII_\alpha$" insert therein --$RII_\beta$--.

In column 14, line 42, delete "$RII_{62}$" insert therein --$RII_\beta$--.

In column 14, line 51, delete "$RII_{62}$" insert therein --$RII_\beta$--.

In column 14, line 58, delete "$RII_{62}$" insert therein --$RII_\beta$--.

In column 14, line 60, delete "$RII_{62}$" insert therein --$RII_\beta$--.

In column 14, line 61, delete "$RII_{62}$" insert therein --$RII_\beta$--.

In column 15, line 1, delete "$RII_{62}$" insert therein --$RII_\beta$--.

In column 15, line 20, delete "$RII_{62}$" insert therein --$RII_\beta$--.

Signed and Sealed this

Sixth Day of January, 1998

Attest:

BRUCE LEHMAN

*Attesting Officer*    Commissioner of Patents and Trademarks